(12) United States Patent
Furukawa et al.

(10) Patent No.: US 6,410,808 B1
(45) Date of Patent: Jun. 25, 2002

(54) METHOD FOR PRODUCING A FLUOROALCOHOL

(75) Inventors: Yutaka Furukawa; Nobuyuki Kasahara; Kazuya Oharu; Shin Tatematsu, all of Yokohama (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 09/840,072

(22) Filed: Apr. 24, 2001

(30) Foreign Application Priority Data

Apr. 26, 2000 (JP) .................................... 2000-126462

(51) Int. Cl.$^7$ ............................................. C07C 31/34
(52) U.S. Cl. ...................................... 568/842; 568/677
(58) Field of Search ................................ 568/842, 677

(56) References Cited

U.S. PATENT DOCUMENTS

| | | | | |
|---|---|---|---|---|
| 2,868,846 A | * | 1/1959 | Lawlor | |
| 4,001,309 A | * | 1/1977 | Hayashi | |
| 4,590,310 A | * | 5/1986 | Townsend | |
| 5,264,637 A | * | 11/1993 | Yoshida | |

FOREIGN PATENT DOCUMENTS

DE  2318677 A  * 11/1974

* cited by examiner

Primary Examiner—Michael L. Shippen
(74) Attorney, Agent, or Firm—Oblon, Spivak, McClelland, Maier & Neustadt, P.C.

(57) ABSTRACT

A method for producing a fluoroalcohol of the following formula 1a, which comprises reacting a compound of the following formula 1 with water in a liquid phase at a temperature of 150° C. or higher under a gauge pressure of 0.4 MPa or higher:

$$R[CF_2(CH_2)_nX]_p \qquad \text{Formula 1}$$

$$R[CF_2(CH_2)_nOH]_p \qquad \text{Formula 1a}$$

wherein n is an integer of from 1 to 5, X is a chlorine atom, a bromine atom or an iodine atom, p is an integer of at least 1, and R is a p-valent organic group, provided that when p is 1, R may be a hydrogen atom or a halogen atom.

9 Claims, No Drawings

METHOD FOR PRODUCING A FLUOROALCOHOL

The present invention relates to a method for producing a fluoroalcohol having a 1,1-difluoro-3-hydoxypropyl group or the like.

A fluoroalcohol such as $C_aF_{2a+1}(CH_2)_2OH$ (wherein a is an integer of from 1 to 23) having a 1,1-difluoro-3-hydroxypropyl group ($-CF_2CH_2CH_2OH$) in its molecular structure, is a compound useful as an intermediate for e.g. a water and oil repellent, a surfactant or a release agent.

As a method for producing such a fluoroalcohol, a method is known which comprises reacting $C_aF_{2a+1}(CH_2)_2X^1$ (wherein a is as defined above, and $X^1$ is a halogen atom) with an alkali metal hydroxide to obtain $C_aF_{2a+1}(CH_2)_2OH$. However, such a reaction has a problem that an olefin compound of the formula $C_aF_{2a+1}CH=CH_2$ will be formed by a side reaction, whereby the yield of the desired compound decreases. As methods to solve such a problem, the following methods have been proposed wherein a fluoroalkyl iodide or a fluoroalkyl bromide is used as the starting material.

(1) A method wherein it is contacted with fuming sulfuric acid or chlorosulfuric acid to produce a sulfuric acid ester, followed by hydrolysis (JP-B-40-1905, JP-B-58-39135). (2) A method wherein it is contacted with water in the presence of N,N-dimethylformamide (DMF) (JP-B-52-8807). (3) A method wherein it is contacted with water in an organic solvent in the presence of a heavy metal ion catalyst (JP-A-63-22040). (4) A method wherein it is reacted with a betaine compound and water (JP-A-2-142741). (5) A-method wherein it is reacted in a gas phase, if necessary, on a solid acid catalyst having an alkali metal component supported thereon (JP-A-2000-79345).

However, the fuming sulfuric acid or chlorosulfuric acid used in the method (1) has problems such that it is highly corrosive and produces a large amount of byproducts such as dialkylsulfates or chlorides which are hardly hydrolysable. The method (2) has a problem that a formic acid ester of the fluoroalcohol will be formed as a byproduct which is hardly separable by distillation, whereby the purity of the product tends to be low. Further, in order to remove DMF by washing with water, a large amount of waste water will form. There is a further problem that formation of an olefin compound as a byproduct cannot be avoided. The method (3) has a problem that it is a method of using a heavy metal. The method (4) has problems such that the betaine compound is expensive, and recycling is not easy, and it is a method which is disadvantageous from the viewpoint of costs in addition to a problem of the resulting waste liquid. The method (5) has problems such that the useful life of the catalyst is short, and it is difficult to maintain a high conversion and a high selectivity.

The present invention has been made to solve the above problems and provides a method for producing a fluoroalcohol in good yield without using a reagent which is difficult to handle.

The present inventors have found it possible to convert a ($-CF_2(CH_2)_nX$) group to the desired ($-CF_2(CH_2)_nOH$) group simply by reacting it with water under certain conditions.

Namely, the present invention provides a method for producing a fluoroalcohol of the following formula 1a, which comprises reacting a compound of the following formula 1 with water in a liquid phase at a temperature of 150° C. or higher under a gauge pressure of 0.4 MPa or higher:

$$R[CF_2(CH_2)_nX]_p \quad \text{Formula 1}$$

$$R[CF_2(CH_2)_nOH]_p \quad \text{Formula 1a}$$

wherein n is an integer of from 1 to 5, X is a chlorine atom, a bromine atom or an iodine atom, p is an integer of at least 1, and R is a p-valent organic group, provided that when p is 1, R may be a hydrogen atom or a halogen atom.

Now, the present invention will be described in detail with reference to the preferred embodiments.

In the compound of the Formula 1, n is preferably 2 from the viewpoint of the availability of the starting material. Further, X is usually a bromine atom or an iodine atom, but is preferably an iodine atom from the viewpoint of the availability of the starting material and the reactivity. Specific examples of the group of the formula $-CF_2(CH_2)_nX$ may be groups shown in the after-mentioned specific examples.

The symbol p represents the number of groups of the formula $-CF_2(CH_2)_nX$ bonded to R. The group of the formula $-CF_2(CH_2)_nX$ is a group bonded to the p-valent organic group. p is preferably 1 or 2. In the Formula 1, R is a p-valent organic group, and the organic group is a group containing at least one carbon atom. R is a group which undergoes no change as between before and after the reaction of the present invention. Accordingly, the p-valent organic group is preferably a group wherein a structure changeable by the reaction of a present invention is not present, and it is preferably a p-valent organic group wherein a structure of the formula $-CF_2(CH_2)_nX$, an ester bond or an amide bond is not present.

Further, the p-valent organic group is preferably a p-valent saturated hydrocarbon group or a p-valent halogenated saturated hydrocarbon group, and from the viewpoint of the easy availability of the compound of the Formula 1, a p-valent halogenated saturated hydrocarbon group is particularly preferred. The p-valent halogenated saturated hydrocarbon group is preferably a p-valent fluorinated saturated hydrocarbon group, particularly preferably a group having all hydrogen atoms in a p-valent saturated hydrocarbon group substituted by fluorine atoms (i.e. a p-valent perfluoro saturated hydrocarbon group). R may have a straight chain structure or a branched chain structure, or a structure partially having a ring structure.

In a case where p in the Formula 1 is 1, R may be a monovalent organic group, a hydrogen atom or a halogen atom, and it is preferably a monovalent organic group or a halogen atom. As the monovalent organic group, an alkyl group, a halogenated alkyl group or a halogenated (etheric oxygen atom-containing alkyl) group is preferred, and particularly preferred is a perfluoroalkyl group or a perfluoro (etheric oxygen atom-containing alkyl) group.

Further, the compound of the Formula 1 is preferably a compound of the following Formula 2, a compound of the following formula 3 or a compound of the following Formula 4, whereby the objective compound is useful and excellent in the reactivity.

$$C_mF_{2m+1}(CH_2)_nX \quad \text{Formula 2}$$

$$X(CH_2)_n(CF_2)_k(CH_2)_nX \quad \text{Formula 3}$$

-continued $$F[CF(CF_3)CF_2O]_rCF_2CF_2(CH_2)_nX \quad \text{Formula 4}$$

wherein n and X are as defined above, m is an integer of from 1 to 18, preferably an integer of from 6 to 16, k is an integer of from 1 to 10, preferably an integer of from 3 to 8, and r is an integer of from 1 to 10, preferably an integer of from 1 to 3.

Further, X in the Formulae 2 and 4, is preferably a bromine atom or an iodine atom, and X in the Formula 3 is preferably an iodine atom. Further, the group of the Formula $C_mF_{2m+1}$— in the Formula 2, preferably has a straight chain structure or a branched structure. In the case of a branched structure, the branched portion is preferably present at the terminal portion of said group, and particularly preferably, it essentially has a $(CF_3)_2CF$— structure.

The following compounds may be mentioned as specific examples of the compound of the Formula 1.

$CF_3(CF_2)_5CH_2I$,
$CF_3CH_2CH_2I$,
$CF_3(CF_2)_7CH_2I$,
$CF_3(CF_2)_2CH_2CH_2I$,
$CF_3(CF_2)_5CH_2CH_2I$,
$CF_3(CF_2)_7CH_2CH_2I$,
$CF_3(CF_2)_9CH_2CH_2I$,
$CF_3(CF_2)_{11}CH_2CH_2I$,
$(CF_3)_2CF(CF_2)_4CH_2CH_2I$,
$CF_3(CF_2)_7CH_2CH_2Br$,
$ICH_2CH_2(CF_2)_4CH_2CH_2I$,
$ICH_2CH_2(CF_2)_6CH_2CH_2I$,
$BrCH_2CH_2(CF_2)_6CH_2CH_2Br$,
$F[CF(CF_3)CF_2O]_3CF_2CF_2CH_2CH_2I$.

These compounds are either known compounds or readily available by known production methods disclosed in e.g. J. Org. Chem., 23, 1166 (1958).

In the present invention, the compound of the Formula 1 is reacted with water in a liquid phase at a temperature of 150° C. or higher under a gauge pressure of 0.4 MPa or higher. The reaction of the present invention can be carried out by a method wherein water and the starting material are charged into an autoclave, and they are subjected to certain specific high temperature high pressure conditions, or a method wherein water is charged into a reactor, and the compound of the formula 1 and water are continuously or intermittently added, while the fluoroalcohol of the Formula 1a and water are continuously or intermittently withdrawn.

The reaction of the present invention is characterized in that the reaction is carried out in a liquid phase using high temperature high pressure water, and the reaction is a so-called subcritical reaction. Further, the reaction of the present invention is preferably carried out at a reaction temperature of at least 150° C. and less than 375° C. and under a pressure of at least the vapor pressure of water at the reaction temperature (i.e. a gauge pressure of from 0.4 to 22.1 MPa), particularly preferably at a reaction temperature of from 180 to 300° C. and under a gauge pressure of from 1 to 10 MPa. If the reaction temperature and the reaction pressure become too high, a supercritical state will result, whereby the reaction cannot be carried out in a liquid phase, and the decomposition reaction of the starting material is likely to take place, whereby there will be a problem that formation of byproducts will increase. On the other hand, if the reaction temperature and the reaction pressure are too low, there will be a problem that the reaction rate decreases.

The reaction time varies depending upon the temperature, but it is preferably from 0.1 to 20 hours, particularly preferably from 0.5 to 10 hours. When the reaction is carried out by a method of continuously or semicontinuously supplying and withdrawing the starting material and the product, respectively, the reaction time (the retention time) is preferably from 0.01 to 3 hours.

When the compound of the Formula 1 is reacted with water, the water serves not only as a reaction substrate but also as a reaction medium, whereby the reaction of the present invention will smoothly be carried out. Further, in the reaction of the present invention, it is preferred to prevent a side reaction from taking place in a gas phase, the amount of water is preferably an amount such that the entire amount of water would not be vaporized under the reaction conditions of the present invention. A more preferred amount of water is such that the reactor is sufficiently filled with water. The amount of water is stoichiometrically one mol per mol of X in the compound of the Formula 1, but it is preferred to use water in an excess amount to X. In a usual case, the amount of water is preferably at least 10 mols, more preferably from 10 to 10,000 mols, per mol of X. The amount of water to be used for the reaction, may be suitably selected taking into consideration also an economical viewpoint such as the apparatus for the reaction.

If the compound of the Formula 1 and water are present in the reaction system for the reaction of the present invention, the desired reaction will usually proceed sufficiently. However, for the purpose of smoothly carrying out the reaction, an additive other than the compound of the Formula 1 and water may be present in the reaction system, as the case requires. Such an additive may, for example, be an acid scavenger added for the purpose of capturing HX (wherein X has the same meaning as in the Formula 1) formed as a byproduct by the reaction. The acid scavenger may, for example, be a metal oxide such as iron oxide, zinc oxide or copper oxide, or a metal such as zinc or iron. Such an additive may be present in the reaction solution or may be present in a gas section within the reactor to capture HX formed at the gas section.

Further, the reaction of the present invention is preferably carried out in the absence of an organic solvent in the reaction system. As the reaction can be carried out in the absence of any organic solvent, the reaction of the present invention is advantageous from the viewpoint of the environment, and formation of byproducts derived from a solvent can be eliminated. Further, it is advantageous that it is unnecessary to remove a solvent during post treatment.

By the reaction of the present invention, the compound of the Formula 1 will react with water to form a compound of the Formula 1a. In the Formula 1a, n, p and R are the same as n, p and R in the Formula 1, respectively. When the compound of the Formula 2 is used as the compound of the Formula 1, a compound of the following Formula 2a will be formed, and when the compound of the Formula 3 is used, a compound of the following Formula 3a will be formed. Likewise, when the compound of the Formula 4 is used, a compound of the following Formula 4a will be formed. In the Formulae 2a, 3a and 4a, m, n, k and r have the same meanings as in the corresponding Formulae 2, 3 and 4, respectively.

$$C_mF_{2m+1}(CH_2)_nOH \quad \text{Formula 2a}$$

$$HO(CH_2)_n(CF_2)_k(CH_2)_nOH \quad \text{Formula 3a}$$

-continued $$F[CF(CF_3)CF_2O]_xCF_2CF_2(CH_2)_nOH \quad \text{Formula 4a}$$

The following compounds may be mentioned as specific examples of the compound of the Formula 1a.

$CF_3(CF_2)_5CH_2OH$,
$CF_3CH_2CH_2OH$,
$CF_3(CF_2)_7CH_2OH$,
$CF_3(CF_2)_3CH_2CH_2OH$,
$CF_3(CF_2)_5CH_2CH_2OH$,
$CF_3(CF_2)_7CH_2CH_2OH$,
$CF_3(CF_2)_9CH_2CH_2OH$,
$CF_3(CF_2)_{11}CH_2CH_2OH$,
$(CF_3)_2CF(CF_2)_4CH_2CH_2OH$,
$CF_3(CF_2)_7CH_2CH_2OH$,
$HOCH_2CH_2(CF_2)_4CH_2CH_2OH$,
$HOCH_2CH_2(CF_2)_6CH_2CH_2OH$,
$HOCH_2CH_2(CF_2)_6CH_2CH_2OH$,
$F[CF(CF_3)CF_2O]_3CF_2CF_2CH_2CH_2OH$.

The product of the above reaction may be employed as it is in the subsequent reaction. However, in a usual case, it is preferably purified to a high purity. As the purification method, a means such as distillation, steam distillation, extraction, recrystallization or column chromatography may be mentioned.

The method of the present invention may be a method wherein a substance having a group of the following Formula 5 is reacted with water in a liquid phase under the same high temperature high pressure conditions to form a substance having a group of the following Formula 5a. The substance having a group of the Formula 5 may be, in addition to the compound of the above Formula 1, a carrier or membrane having groups of the Formula 5 bonded thereto. From the carrier or membrane having the groups of the Formula 5 bonded thereto, a carrier or membrane having the groups of the following Formula 5a bonded thereto will form. In this case, the production conditions, etc., are the same as the conditions in the case of the compound of the Formula 1.

$$—CF_2(CH_2)_nX \quad \text{Formula 5}$$

$$—CF_2(CH_2)_nOH \quad \text{Formula 5a}$$

The compound of the Formula 1a obtainable by the method of the present invention, is a compound useful as an intermediate for e.g. a water and oil repellent, a surfactant, a release agent or a pharmaceutical or agricultural chemical.

The mechanism of the reaction of the present invention is not clearly understood, but it is considered that under the conditions of the present invention, water at a high temperature under a high pressure, will increase the ion product and will serve as an electrolyte solvent, whereby an ionic reaction to hydrolyze $—CF_2(CH_2)_nX$, will take place.

Now, the present invention will be described in further detail with reference to Examples. However, it should be understood that the present invention is by no means restricted to such specific Examples.

Examples 1 to 4 are working examples of the present invention, and Example 5 is a comparative example.

EXAMPLE 1

Into a deaerated autoclave made of Hastelloy C22 and having an internal capacity of 66 ml, $CF_3(CF_2)_7(CH_2)_2I$ (0.5 g) and deionized water (20 g) were charged, then the temperature was raised to 300° C., and the reaction was carried out for 4 hours under a gauge pressure of 9.2 MPa.

After completion of the reaction, ethyl ether (20 ml) was put into the reaction mixture. After separation into two layers, to the ethyl ether layer, magnesium sulfate (0.2 g) was put, and then magnesium sulfate was removed by filtration to obtain a product. Identification of the product was carried out by $^1$H-NMR and $^{19}$F-NMR, and the quantitative analysis of the product was carried out by gas chromatography (hereinafter referred to as GC), whereby the conversion of $CF_3(CF_2)_7(CH_2)_2I$ was 91%, and the selectivity for $CF_3(CF_2)_7(CH_2)_2OH$ was 70%.

EXAMPLE 2

The reaction was carried out in the same manner as in Example 1 except that $CF_3(CF_2)_7(CH_2)_2I$ was 2 g, the deionized water was 40 g, the reaction temperature was changed to 270° C., and the gauge pressure was changed to 6.3 MPa. The product was analyzed, whereby the conversion of $CF_3(CF_2)_7(CH_2)_2I$ was 83%, and the selectivity for $CF_3(CF_2)_7(CH_2)_2OH$ was 85%.

EXAMPLE 3

Into a deaerated autoclave made of Hastelloy C22, having an internal capacity of 66 ml and equipped with a stirrer, 0.5 g of $CF_3(CF_2)_7(CH_2)_2I$ and 55 g of deionized water were charged, then, the temperature was raised to 270° C,, and the reaction was carried out for 4 hours under a gauge pressure of 6.3 MPa at a stirring rotational speed of 250 rpm.

After completion of the reaction, ethyl ether (20 ml) was put into the reaction mixture. After separation into two layers, magnesium sulfate (0.2 g) was put into the ethyl ether layer, and then magnesium sulfate was removed by filtration to obtain a product. Identification of the product was carried out by $^1$H-NMR and $^{19}$F-NMR, and the quantitative analysis of the product was carried out by GC, whereby the conversion of $CF_3(CF_2)_7(CH_2)_2I$ was 99%, and the selectivity for $CF_3(CF_2)_7(CH_2)_2OH$ was 91%.

EXAMPLE 4

The reaction was carried out in the same manner as in Example 3 except that $CF_3(CF_2)_7CH_2CH_2I$ was changed to 1 g. The product was analyzed, whereby the conversion of $CF_3(CF_2)_7CH_2CH_2I$ was 99%, and the selectivity for $CF_{30}(CF_2)_7CH_2CH_2OH$ was 96%.

EXAMPLE 5

$CF_3(CF_2)_7CH_2CH_2I$ (52 g), DMF (47 g) and water (2.5 g) were charged into a 200 ml shaking tube and shaked for 6 hours at 140° C. Then, water (12 g) was added, followed by shaking for further 12 hours at 110° C. The reaction mixture was cooled to 50° C, and then washed with water (50 ml), to obtain an oil layer as the product. The product was analyzed by GC, whereby the conversion of $CF_3(CF_2)_7CH_2CH_2I$ was 99%, and the selectivity for $CF_3(CF_2)_7CH_2CH_2OH$ was 65% and the selectivity for $CF_3(CF_2)_7CH_2CH_2OCOH$ was 5%. Further, in the product, 20% of $CF_3(CF_2)_7CH=CH_2$ was contained as a byproduct, and DMF was also contained in a large amount. Further, it was attempted to remove DMF by washing with water (100 ml) of 90° C. for four times, but DMF still remained in an amount of 0.5% in the product.

According to the present invention, a reaction substrate and water as a solvent for the reaction are employed, and they are reacted under certain specific high temperature high pressure conditions, whereby the desired fluoroalcohol can be produced. Further, according to the method of the present invention, the fluoroalcohol can be obtained in good yield. The reaction of the present invention can be carried out without using a reagent which is difficult to obtain or to handle or an expensive reagent, and thus, it is an excellent method which can be adopted as an industrial method. Further, the method of the present invention can be carried out without using any organic solvent, whereby it is unnecessary to carry out treatment of a waste liquid, and thus it is an environmentally advantageous method.

The entire disclosure of Japanese Patent Application No. 2000-126462 filed on Apr. 26, 2000 including specification, claims, drawings and summary are incorporated herein by reference in its entirety.

What is claimed is:

1. A method for producing a fluoroalcohol of the following formula 1a, consisting essentially of reacting a compound of the following formula 1 with water in a liquid phase at a temperature of 150° C. or higher under a gauge pressure of 0.4 MPa or higher:

$$R[CF_2(CH_2)_nX]_p \qquad \text{Formula 1}$$

$$R[CF_2(CH_2)_nOH]_p \qquad \text{Formula 1a}$$

wherein n is an integer of from 1 to 5, X is a chlorine atom, a bromine atom or an iodine atom, p is an integer of at least 1, and R is a p-valent organic group, provided that when p is 1, R may be a hydrogen atom or a halogen atom.

2. The method according to claim 1, wherein the compound of the formula 1 is a compound of the following formula 2, and the compound of the formula 1a is a compound of the following formula 2a:

$$C_mF_{2m+1}(CH_2)_nX \qquad \text{Formula 2}$$

$$C_mF_{2m+1}(CH_2)_nOH \qquad \text{Formula 2a}$$

wherein m is an integer of from 1 to 18, and n and X are as defined above.

3. The method according to claim 1, wherein the compound of the formula 1 is a compound of the following formula 3, and the compound of the formula 1a is a compound of the following formula 3a:

$$X(CH_2)_n(CF_2)_k(CH_2)_nX \qquad \text{Formula 3}$$

$$HO(CH_2)_n(CF_2)_k(CH_2)_nOH \qquad \text{Formula 3a}$$

wherein k is an integer of from 1 to 10, and n and X are as defined above.

4. The method according to claim 1, wherein the compound of the formula 1 is a compound of the following formula 4, and the compound of the formula 1a is a compound of the following formula 4a:

$$F[CF(CF_3)CF_2O]_rCF_2CF_2(CH_2)_nX \qquad \text{Formula 4}$$

$$F[CF(CF_3)CF_2O]_rCF_2CF_2(CH_2)_nOH \qquad \text{Formula 4a}$$

wherein r is an integer of from 1 to 10, and n and X are as defined above.

5. The method according to claim 1, wherein the reaction is carried out at a temperature of from 150 to 340° C. under a gauge pressure of from 0.4 to 22.1 MPa.

6. The method according to claim 1, wherein the reaction is carried out without using an organic solvent.

7. A method for producing a fluoroalcohol having a group of the following formula 5a, consisting essentially of reacting a compound having a group of the following formula 5 with water in a liquid phase at a temperature of 150° C. or higher under a gauge pressure of 0.4 MPa or higher:

$$-\!\!-\!\!CF_2(CH_2)_nX \qquad \text{Formula 5}$$

$$-\!\!-\!\!CF_2(CH_2)_nOH \qquad \text{Formula 5a}$$

wherein n is an integer of from 1 to 5, and X is a chlorine atom, a bromine atom or an iodine atom.

8. The method according to claim 7, wherein the reaction is carried out at a temperature of from 150 to 340° C. under a gauge pressure of from 0.4 to 22.1 MPa.

9. The method according to claim 7, wherein the reaction is carried out without using an organic solvent.

* * * * *